United States Patent [19]
Thiele

[11] Patent Number: 5,675,026
[45] Date of Patent: Oct. 7, 1997

[54] PROCESS FOR THE PRODUCTION OF EPOXIDES FROM OLEFINS

[75] Inventor: Georg Thiele, Hanau, Germany

[73] Assignee: DeGussa Aktiengesellschaft, Frankfurt, Germany

[21] Appl. No.: 668,451

[22] Filed: Jun. 21, 1996

[30] Foreign Application Priority Data

Aug. 1, 1995 [DE] Germany .......... 195 28 219.1

[51] Int. Cl.$^6$ .......... C07D 301/12
[52] U.S. Cl. .......... 549/531
[58] Field of Search .......... 549/531

[56] References Cited

U.S. PATENT DOCUMENTS

| 4,824,976 | 4/1989 | Clerici et al. | 549/531 |
| 5,412,122 | 5/1995 | Saxton et al. | 549/531 |

FOREIGN PATENT DOCUMENTS

| 230949 | 8/1987 | European Pat. Off. | 549/531 |

Primary Examiner—C. Warren Ivy
Assistant Examiner—Lyman H. Smith
Attorney, Agent, or Firm—Cushman Darby & Cushman IP Group of Pillsbury Madison & Sutro

[57] ABSTRACT

Process for the production of epoxides from olefins and hydrogen peroxide in the presence of a zeolite containing titanium atoms as catalyst, to which neutral- or acid-reactive salts are added before or during the reaction.

16 Claims, 3 Drawing Sheets

PROCESS FOR THE PRODUCTION OF EPOXIDES FROM OLEFINS

BACKGROUND OF THE INVENTION

1. Field of the Invention

The invention relates to a process for the production of epoxides from olefins.

2. Prior Art

It is known to produce epoxides by reaction of olefins with hydrogen peroxide in the presence of titanium silicalite TS1 (EP-A 0 100 119). The known process has the disadvantage that the epoxide yield is reduced by acid-catalyzed subsequent reactions of the epoxide with water or with the solvent present in the reaction mixture, which are brought about by the weakly acidic titanium silicalite TS1.

It is known furthermore to produce epoxides by reaction of olefins with hydrogen peroxide in the presence of a titanium silicalite TS1 pretreated with bases (EP-A 0 230 949). In this process the amounts of bases used for the neutralization of the catalyst (titanium silicalite TS1) must be selected within narrow limits, since an exceeding of the limit leads to a severe loss of activity of the catalyst (M. G. Clerici et al., Journal of Catalysis 140, 71–83 (1993)). The known process has the disadvantage that the treatment with relatively large amounts of bases leads to a severe loss of activity, as far as to the complete inhibition of the reaction.

SUMMARY OF THE INVENTION

The present invention provides a process for the production of epoxides from olefins and hydrogen peroxide in the presence of a titanium atom-containing zeolite as catalyst, which is characterized in that before or during the reaction neutral- or acid-reactive salts are added to the catalyst.

The neutral- or acid-reactive salt can contain one or more cations from the group $Li^+$, $Na^+$, $K^+$, $NH_4^+$, $RNH_3^+$ or $R_2NH_2^+$, wherein R represents an alkyl group with 1 to 6 carbon atoms.

As the neutral- or acid-reactive salt, a salt of the composition $M^+X^-$ or of the composition $M_2SO_4$ can preferably be used, wherein $M^+$ represents $Li^+$, $Na^+$, $K^+$ or $NH_4^+$ and $X^-$ represents $NO_3^-$, $ClO_4^-$, $Cl^-$ or $H_2PO_4^-$.

In one embodiment of the invention, the catalyst containing titanium atoms is reacted before its use for the epoxidation with a solution of a neutral- or acid-reactive salt in water or an alcohol, separated from this solution, optionally washed with water and/or a solvent and subsequently used for the epoxidation of an olefin. The concentration of the salt solution used for the treatment of the catalyst can be varied between 0.0001 mol/l and the saturation limit, preferably between 0.01 and 1 mol/l, wherein in contrast to the prior art even concentrations of 0.1 mol/l and higher have no unfavorable effects on the catalytic activity of the treated catalyst in the oxidation reaction. Temperature and duration of the catalyst treatment may be selected within wide limits and are only restricted by the rate of mass transfer between catalyst and salt solution at low temperature and short treatment time and the stability of the catalyst towards hydrolysis at high temperature and long treatment times. The salt solution used for the treatment of the catalyst can advantageously be reused repeatedly, the number of possible reuses being dependent on the concentration of the salt solution and the quantitative ratio of salt solution to treated catalyst.

In another embodiment of the invention, the treatment of the catalyst is carried out during the epoxidation reaction. For this purpose the salt, optionally as a solution in water or another solvent, is added either directly to the reaction mixture of the epoxidation or to one of the materials used in the epoxidation reaction. The amount of salt can then be chosen so that the salt concentration in the reaction mixture is between 0.0001 and 1 mol/l, preferably between 0.001 and 1 mol/l. The neutral- or acid-reactive salt can advantageously also be added to the hydrogen peroxide used for the epoxidation without having an unfavourable effect on its stability in storage.

In a continuous embodiment of the epoxidation reaction, the treatment according to the invention can be carried out both by a continuous and by an intermittent addition of the salt used for the catalyst treatment.

The epoxidation of olefins with hydrogen peroxide in the presence of a catalyst containing titanium atoms, which is treated before or during the epoxidation reaction with a neutral or acid water-soluble salt, has the advantage over known processes that with reduced by-product formation a variation of the amount of the substance used for the treatment of the catalyst does not have an unfavourable effect on the catalytic activity of the catalyst during the epoxidation reaction.

The process according to the invention can be applied to all olefins that can also be epoxidized with the non-pretreated catalyst. For example, the olefins that are listed in the document EP-A 0 100 119 can be used. Olefins with 2 to 16 carbon atoms that are unbranched or substituted with methyl groups as well as allyl chloride and allyl alcohol, especially propylene, butene-1, butene-2, isobutene or pentene-1 can preferably be used.

The following known compounds can be used as zeolites containing titanium atoms: titanium silicalite-1 with MFI structure, titanium silicalite-2 with MEL structure, titanium beta-zeolite, TS-48 with the structure of zeolite ZSM-48 as well as titanium mordenite with the MOR structure. These zeolites are known from the following literature:

Titanium silicalite-1 (TS1) DE 30 47 798

Titanium silicalite-2 (TS2) BE 1 001 038; J. S. Reddy, R. Kumar, P. Ratnasamy, Appl. Catal. 58 (1990) L1

Titanium beta-zeolite ES 2 037 596, M. A. Camblor, (Ti-beta) A. Corma, A. Martinez, J. Perez-Pariente, J. Chem. Soc., Chem. Commun. 1992, 589

TS-48 D. P. Serrano, H. X. Li, M. E. Davis, J. Chem. Soc., Chem. Commun. 1992, 745

Titanium mordenite G. J. Kim, B. R. Cho, J. H. Kim, Catal. Letters 1993, 259

Preferably titanium silicalite-1 and titanium silicalite-2 are used, and most preferably titanium silicalite-1.

DETAILED DESCRIPTION OF PREFERRED EMBODIMENTS OF THE INVENTION

EXAMPLES

Figure 1:
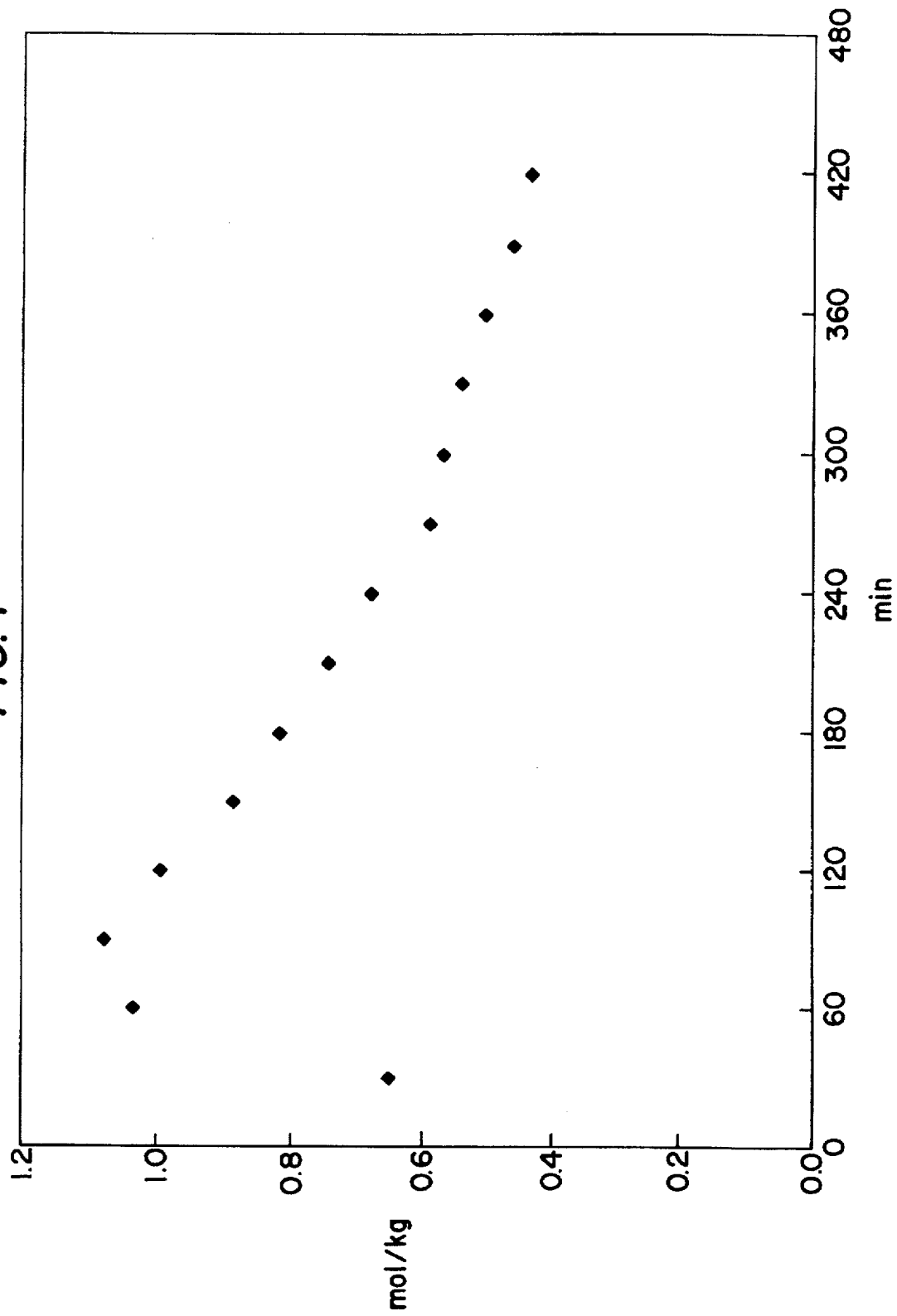
FIGS. 1–3 illustrate the concentration of reaction products at the reactor outlet for selected examples of the invention.

For the following examples, three samples of titanium silicalite are used, which are prepared according to the information in J. P. A. Martens et al., Appl. Catal. A 99 (1993) 71–84 and are designated below as Catalysts 1, 2 and 3.

Example 1

Determination of the catalytic activity of titanium silicalite in the epoxidation of propylene with hydrogen peroxide 1 g Catalyst 1 in 300 ml methanol are charged at 40° C. under propylene atmosphere to a thermostated laboratory autoclave with gas-dispersing stirrer and saturated with propylene at an excess pressure of 3 bar. Then 13.1 g 30 wt.

% aqueous hydrogen peroxide solution are added in one portion with stirring and the reaction mixture is maintained at 40° C. and 3 bar, propylene being subsequently added in doses via a pressure regulator in order to compensate the consumption by the reaction. Samples are taken at regular intervals via a filter and the hydrogen peroxide content of the reaction mixture is determined by redox titration with cerium(IV) sulphate solution. The plotting of in ($c/c_0$) against the time t, where c is the measured $H_2O_2$ concentration at the time t and $c_0$ the calculated $H_2O_2$ concentration at the start of the reaction, yields a straight line. From the gradient of the straight line, with the equation $dc/dt=-k.c.c_{cat}$, where $c_{cat}$ represents the catalyst concentration in kg catalyst per kg reaction mixture, the activity index k is determined as 15.0 $min^{-1}$.

Examples 2–4

Catalytic activity of the titanium silicalite treated according to the invention in the epoxidation of propylene 5 g Catalyst 1 are suspended for 4 h at 20° C. in 500 ml of a solution of 0.1 mol/l of a neutral or acidic salt in completely deionized water, then filtered, washed with completely deionized water and methanol, and dried by exposure to air at 20° C. The catalytic activity in the epoxidation of propylene of the catalyst samples thus treated is determined according to Example 1. Table 1 shows the salts used for the treatment of the catalyst and the catalytic activities of the treated catalyst samples.

TABLE 1

Catalytic activity of titanium silicalite in the epoxidation of propylene after treatment with neutral or acidic salts.

| Example | Salt used for treatment | Activity index in $min^{-1}$ |
|---|---|---|
| 1 | — | 15.0 |
| 2 | $Na_2SO_4$ | 16.4 |
| 3 | $(NH_4)_2SO_4$ | 11.7 |
| 4 | $NH_4NO_3$ | 9.4 |

Comparative Examples 5–8

Catalytic activity of titanium silicalite treated with bases according to the prior art in the epoxidation of propylene.

Examples 2–4 are repeated, but instead of the neutral or acidic salt a solution containing 0.1 mol/l of a base in completely deionized water is used for the treatment of the catalyst. Table 2 shows the bases used for the treatment of the catalyst and the catalytic activity of the treated catalyst samples:

TABLE 2

Catalytic activity of titanium silicalite in the epoxidation of propylene after the treatment with bases.

| Example | Base used for treatment | Activity index in $min^{-1}$ |
|---|---|---|
| 1 | — | 15.0 |
| 5 | NaOAc | 2.2 |
| 6 | $NH_4OAc$ | 1.1 |
| 7 | $NH_3$ | 0.3 |
| 8 | NaOH | 0.1 |

Examples 2–4 and Comparative Examples 5–8 show that the treatment according to the invention of the catalyst has only a small effect on the activity of the catalyst in the epoxidation of propylene, while the treatment of the catalyst with bases according to the prior art under otherwise equal conditions causes a large loss in catalytic activity.

Example 9

Determination of by-product formation in the epoxidation of propylene with hydrogen peroxide and a titanium silicalite catalyst Example 1 is repeated with Catalyst 2. The activity index is determined as 23.7 $min^{-1}$. In addition, 2 h after addition of the hydrogen peroxide a sample is taken and the content of the main product propylene oxide and the by-products 1-methoxy-2-propanol, 2-methoxy-1-propanol and 1,2-propanediol determined gas-chromatographically. The proportion of the three by-products in the total amount of products is determined as 8.6 mol %.

Examples 10–12

By-product formation in the epoxidation of propylene with titanium silicalite treated according to the invention Examples 2–4 are repeated with Catalyst 2. The catalytic activity of the treated catalyst samples and the proportion of by-product formation is determined as in Example 9. Table 3 shows the results of Examples 10–12.

Comparative Example 13

By-product formation in the epoxidation of propylene with titanium silicalite treated according to the prior art Comparative Example 5 is repeated with Catalyst 2. The catalytic activity of the neutralized catalyst sample and the proportion of by-products is determined as in Example 9 and is shown in Table 3.

TABLE 3

Catalytic activity and proportion of by-products in the total amount of products in the epoxidation of propylene with pretreated titanium silicalite

| Example | Substance used for the treatment | Activity index in $min^{-1}$ | Proportion of by-products in mol % |
|---|---|---|---|
| 9 | — | 23.7 | 8.6 |
| 10 | $Na_2SO_4$ | 21.4 | 2.6 |
| 11 | $(NH_4)_2SO_4$ | 15.8 | 1.6 |
| 12 | $NH_4NO_3$ | 20.6 | 2.3 |
| 13 | NaOAc | 4.5 | 0.7 |

By comparison with Example 9, Examples 10–12 show that the treatment according to the invention of the catalyst with neutral or acidic salts leads to a considerable reduction of the proportion of by-product formation during the epoxidation of olefins with hydrogen peroxide.

Example 14

Example 1 is repeated with Catalyst 3. The activity index is determined as 21.2 $min^{-1}$.

Example 15

Catalytic activity of titanium silicalite treated with $NaH_2PO_4$ in the epoxidation of propylene.

Examples 2–4 are repeated with Catalyst 3, but $NaH_2PO4$ is used as the acidic salt. The catalytic activity is determined as in Example 1 and is shown in Table 4.

Example 16 (Comparative Example)

Catalytic activity of titanium silicalite neutralized with $Na_2HPO_4$ in the epoxidation of propylene.

Examples 5–8 are repeated with catalyst 3, but Na₂HPO4 is used as base. The catalytic activity is determined as in Example 1 and is shown in Table 4

TABLE 4

Catalytic activity of titanium silicalite in the epoxidation
of propylene after treatment with NaH$_2$PO$_4$ or Na$_2$HPO$_4$

| Example | Base used for treatment | Activity index in min$^{-1}$ |
|---|---|---|
| 14 | — | 21.2 |
| 15 | NaH$_2$PO$_4$ | 12.7 |
| 16 | Na$_2$HPO$_4$ | 0.3 |

Example 15 and Comparative Example 16 show that the treatment according to the invention of the catalyst with the acid-reactive salt NaH$_2$PO$_4$ only slightly affects the activity of the catalyst in the epoxidation of propylene. Compared with that, the treatment of the catalyst with the basic-reactive salt Na$_2$HPO$_4$ under otherwise the same conditions causes a large loss of catalytic activity.

Example 17

Catalytic activity of titanium silicalite in the continuous epoxidation of propylene 5 g catalyst 3 are charged in 295 g methanol at 40° C. under a propylene atmosphere to a thermostated laboratory autoclave with gas-dispersing stirrer and saturated with propylene at an excess pressure of 3 bar. Then, while stirring, a mixture of 475 g 50 wt % hydrogen peroxide, 2225 g methanol and 560 g completely deionized water is charged at a rate of 300 g/h and simultaneously as much reaction mixture removed via a filter that the weight of the reactor contents remains constant. During this, the catalyst is retained in the reactor by the filter. During the addition of hydrogen peroxide, more propylene is added via a pressure controller in order to maintain the pressure at a constant level in the reactor. Samples are taken at the reactor outlet at regular intervals and the content of reaction products (propylene oxide, 1-methoxy-2-propanol and 2-methoxy-1-propanol) determined by gas chromatography. FIG. 1 shows the concentration of reaction products at the reactor outlet in mol/kg against the time in min.

Example 18

Figure 2:
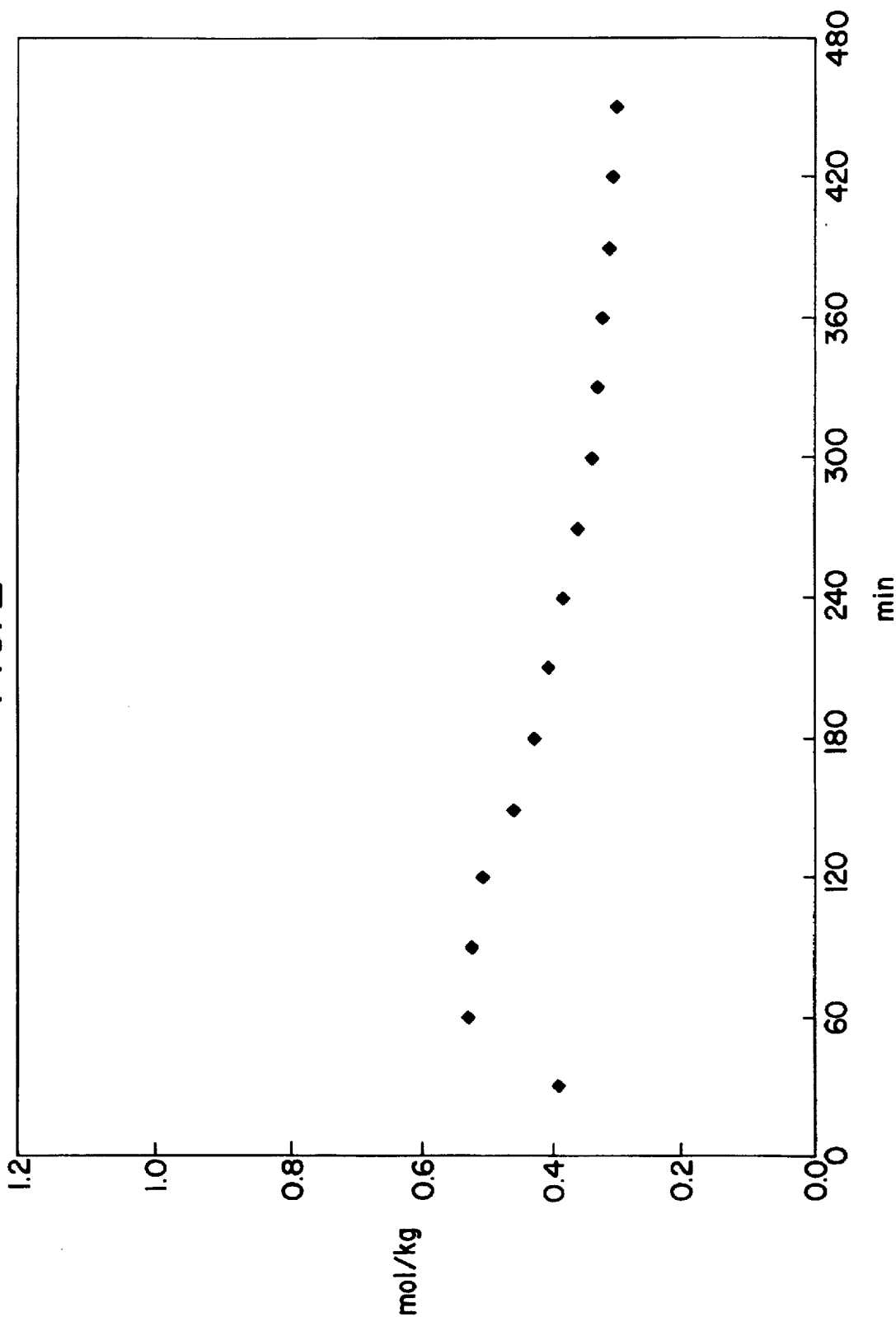

Catalytic activity of titanium silicalite treated according to the invention in the continuous epoxidation of propylene Example 17 is repeated. However, an additional 0.1 mol/kg ammonium nitrate is added to the mixture of methanol, water and hydrogen peroxide. FIG. 2 shows the concentration of reaction products at the reactor outlet in mol/kg against the time in min.

Comparative Example 19

Figure 3:
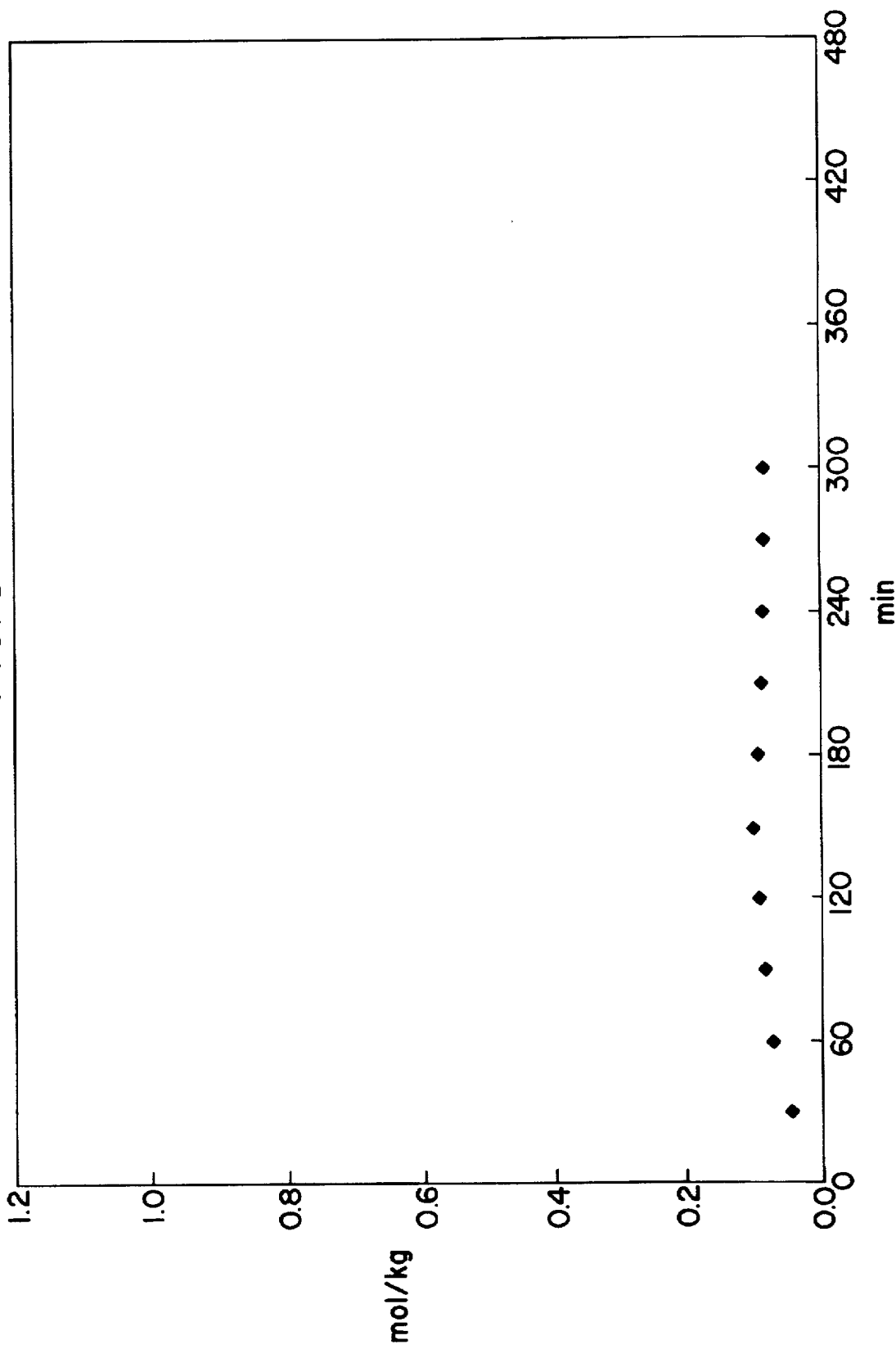

Catalytic activity of titanium silicalite neutralized according to the prior art in the continuous epoxidation of propylene Example 17 is repeated. However, an additional 0.1 mol/kg lithium acetate is added to the mixture of methanol, water and hydrogen peroxide. The concentration of reaction products at the reactor outlet in mol/kg against the time in min. is shown in FIG. 3.

Examples 17 and 18 and Comparative Example 19 show that under otherwise the same conditions the treatment of the catalyst according to the invention has a less unfavourable effect on the activity of the catalyst in the continuous epoxidation of propylene than the treatment of the catalyst with bases according to the prior art.

What is claimed is:

1. A process for the production of epoxides from olefins and hydrogen peroxide in the presence as catalyst of a zeolite containing titanium silicalite-1 (TS1) or titanium silicalite-2 (TS2), wherein neutral or acidic salts are added to the catalyst before or during the reaction.

2. A process according to claim 1, wherein the salt used for the treatment of the catalyst contains one or more cations from the group Li⁺, Na⁺, K⁺, NH$_4^+$, RNH$_3^+$ or R$_2$NH$_2^+$, wherein R represents an n-alkyl group with 1 to 6 carbon atoms.

3. A process according to claim 1 or 2, wherein for the treatment of the catalyst a salt of the composition M⁺X$^{31}$ is used, wherein M⁺ represents Li⁺, Na⁺, K⁺ or NH$_4^+$ and X⁻ represents NO$_3^-$, ClO$_4^-$, Cl⁻ or H$_2$PO$_4^-$.

4. A process according to claim 1 or 2, wherein for the first treatment of the catalyst a salt of the composition M$_2$SO$_4$ is used, wherein the salt cation is selected from Li⁺, Na⁺, K⁺ or NH$_4^+$.

5. A process according to claim 1 or 2, wherein the catalyst is treated with an aqueous or alcoholic solution of the salt.

6. A process according to claim 5, wherein the catalyst, before its use for the epoxidation, is treated with the salt solution and the salt solution used for the treatment is reused repeatedly for the treatment of fresh quantities of catalyst.

7. A process according to claim 5, wherein the catalyst is treated by the addition of the salt solution to the epoxidation reaction.

8. A process according to claim 3, wherein the catalyst is treated with an aqueous or alcoholic solution of the salt.

9. A process according to claim 8, wherein the catalyst, before its use for the epoxidation, is treated with the salt solution and the salt solution used for the treatment is reused repeatedly for the treatment of fresh quantities of catalyst.

10. A process according to claim 8, wherein the catalyst is treated by the addition of the salt solution to the epoxidation reaction.

11. A process according to claim 4, wherein the catalyst is treated with an aqueous or alcoholic solution of the salt.

12. A process according to claim 11, wherein the catalyst, before its use for the epoxidation, is treated with the salt solution and the salt solution used for the treatment is reused repeatedly for the treatment of fresh quantities of catalyst.

13. A process according to claim 11, wherein the catalyst is treated by the addition of the salt solution to the epoxidation reaction.

14. Process according to one of claim 1 or 2, wherein the salt used for the treatment of the catalyst is added to one of the feed materials of the epoxidation reaction.

15. A process according to claim 3, wherein the salt used for the treatment of the catalyst is added to one of the feed materials of the epoxidation reaction.

16. A process according to claim 4, wherein the salt used for the treatment of the catalyst is added to one of the feed materials of the epoxidation reaction.

* * * * *